(12) United States Patent
Landuyt

(10) Patent No.: US 6,387,076 B1
(45) Date of Patent: May 14, 2002

(54) CATHETER RETAINERS AND ASSEMBLIES

(75) Inventor: Christophe Van Landuyt, London (GB)

(73) Assignee: Smith Group PLC, London (GB)

( * ) Notice: Subject to any disclaimer, the term of this patent is extended or adjusted under 35 U.S.C. 154(b) by 0 days.

(21) Appl. No.: 09/440,695

(22) Filed: Nov. 16, 1999

(30) Foreign Application Priority Data

Nov. 28, 1998 (GB) .............................................. 9826045
Mar. 19, 1999 (GB) .............................................. 9906383

(51) Int. Cl.[7] .............................................. A61M 5/32
(52) U.S. Cl. .................................. 604/174; 128/DIG. 6
(58) Field of Search .................................. 604/171, 174, 604/177, 178–180, 264, 523; 128/DIG. 6, DIG. 26

(56) References Cited

U.S. PATENT DOCUMENTS

| 4,193,174 A | * | 3/1980 | Stephens |
| 4,360,025 A | * | 11/1982 | Edwards |
| 4,397,647 A | * | 8/1983 | Gordon |
| 4,659,329 A | * | 4/1987 | Annis |
| 4,898,587 A | | 2/1990 | Mera |
| 5,226,892 A | * | 7/1993 | Boswell |
| 5,389,082 A | | 2/1995 | Baugues et al. |
| 5,795,335 A | | 8/1998 | Zinreich |

FOREIGN PATENT DOCUMENTS

| EP | 0 389 247 | 9/1990 |
| EP | 0 422 631 | 4/1991 |
| EP | 0 567 029 | 10/1993 |
| GB | 2115290 | 9/1983 |
| WO | WO 96/10435 | 4/1996 |
| WO | WO 99/20334 | 4/1999 |
| WO | WO 99/59665 | 11/1999 |

* cited by examiner

Primary Examiner—Brian L. Casler
Assistant Examiner—LoAn H. Thanh
(74) Attorney, Agent, or Firm—Connolly Bove Lodge & Hutz, LLP

(57) ABSTRACT

An epidural catheter retainer has an integral base and hinged lid. The base is attached to the skin and has a side opening through which the catheter can be inserted sideways into the retainer. A channel extends laterally across the base and has protrusions to grip the catheter. When the lid is closed, it covers the side opening and is held down by a catch. The underside of the lid has teeth or the like to grip the upper side of the catheter so that the retainer isolates that part of the catheter in the body from force exerted on its other end.

12 Claims, 5 Drawing Sheets

CATHETER RETAINERS AND ASSEMBLIES

BACKGROUND OF THE INVENTION

This invention relates to catheter retainers and assemblies.

The invention is more particularly concerned with devices for retaining a catheter in position where it emerges from the patient's skin, and with assemblies including such devices.

Catheter retainers are used to prevent catheters being displaced from position in a patient's body. In one form, they are used with epidural catheters, the retainer being fixed to the patient's skin around the site of entry of the catheter into the body. One example of such a retainer is described in GB2288542. In this device, the epidural catheter enters the device through a hole in the base plate and is clamped in position by a hinged lever. Such an arrangement has a disadvantage because it is necessary to thread one end of the catheter through the hole. This may not be possible to achieve after connection of the catheter to a coupling, making it more difficult to install the retainer at a later stage. It is also relatively difficult to remove the retainer from the skin without disturbing the catheter should it be necessary to inspect the skin around the site of entry of the catheter. If the retainer obscures the site of entry of the catheter on the skin it makes it difficult to check the depth of insertion of the catheter from inspection of its distance markings, since this can only be done at a location spaced from the skin entry site. Other examples of catheter retainers are described in GB2288538; US4645492; GB2147811; US4261363; US4659329; US4360025; US4533349; EP327299; GB2115290; EP648512; GB2234172; "A method of securing epidural catheters" by Schmitt L G and Ullma D A, Anaest Analg 1989: 69: 856–7; "Securing epidural catheters, a modification" by B E Harrington and D J Kopacz, Anaest Analg 1990: 71: 440–6; and "New device for the securement of epidural catheters" by S B Corn and S Datta, Regional Anaesthesia, vol 20, No 6, Nov–Dec 95, 545–546. One form of epidural catheter clamp is sold by SIMS Portex, Inc of Keene, N.H., USA under the trade mark "Sure Snap".

BRIEF SUMMARY OF THE INVENTION

It is an object of the present invention to provide a catheter retainer and assembly including such a retainer.

According to one aspect of the present invention there is provided a catheter retainer having a base arranged for attaching to the skin, the base having a locating region and an opening at its side through which the catheter can be inserted sideways into the retainer along the locating region, and a lid that is closable on the base, and the retainer being arranged to retain the catheter against displacement where it extends through the retainer.

The lid preferably has gripping means on its underside such that the catheter is retained between the locating region and the gripping means. The gripping means may include a plurality of teeth and or alternatively a resilient pad. The locating region may have protrusions adapted to engage the catheter and is preferably formed in a channel in the base. The opening preferably has a narrow entrance that widens to a larger region. The lid may be hinged with the base and arranged to cover the opening when closed. The locating region is preferably located on a path that extends substantially laterally of the base such that the catheter extends laterally across the retainer and emerges from the retainer substantially opposite the opening. The catheter retainer preferably includes a catch adapted to retain the lid closed on the base. The lid and base may be formed as a single-piece moulding.

According to another aspect of the present invention there is provided an assembly of a catheter and a retainer according to the above one aspect of the invention.

Various epidural catheter retainers according to the present invention will now be described, by way of example, with reference to the accompanying drawings.

DETAILED DESCRIPTION OF THE PREFERRED EMBODIMENTS

Figure 1:
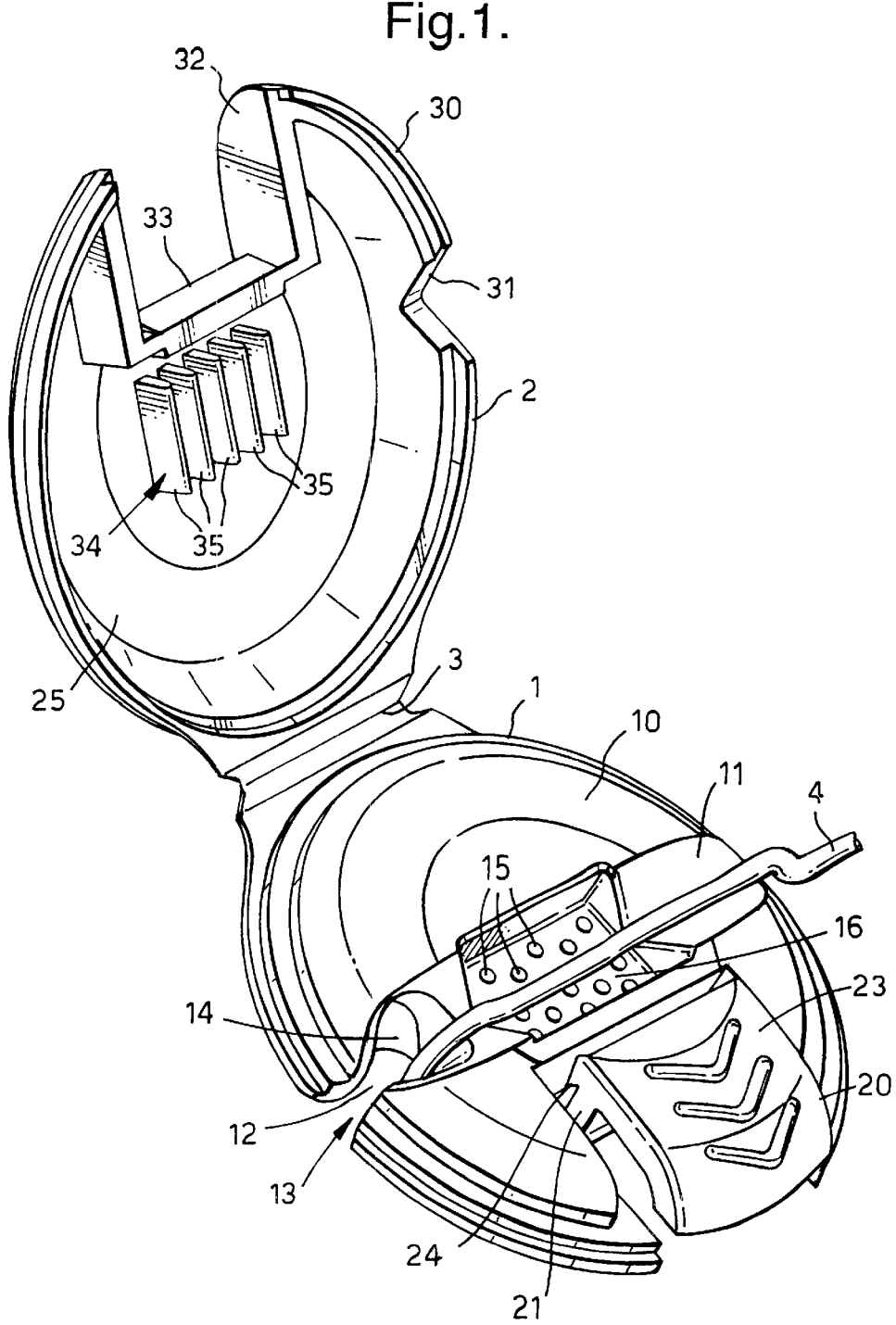
FIG. 1 is a perspective view of a first form of retainer with the lid open.
Figure 2:
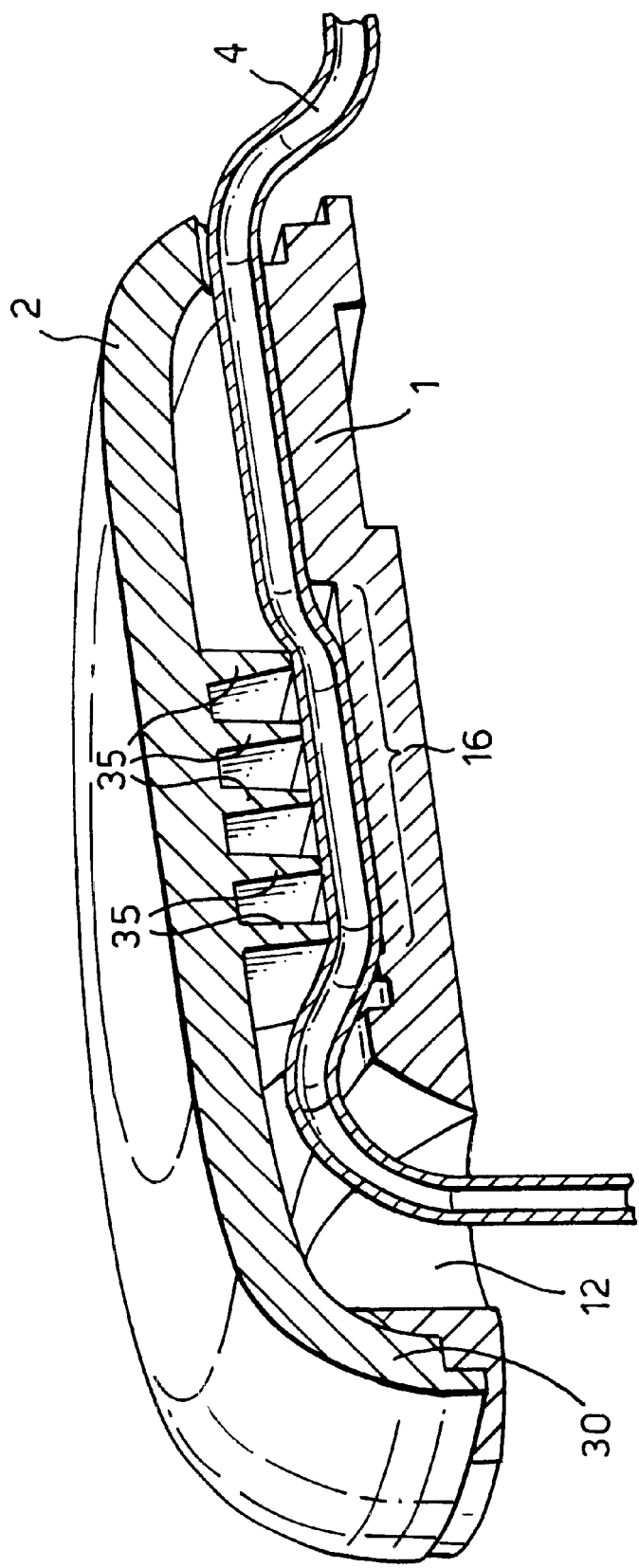
FIG. 2 is a sectional side elevation view across the retainer of FIG. 1 with the lid closed.

With reference first to FIGS. 1 and 2, the retainer is of generally oval shape in plan comprising a base plate 1 and an integral lid 2 hinged with the base plate by a flexible web 3 at one end. The retainer is used to retain an epidural catheter 4 where it emerges from the patient's skin.

The base plate 1 has a domed upper surface 10 and a transverse recessed channel 11 extending laterally across the plate parallel with the hinge line of the lid 2. The left-hand end of the channel 11 extends to a slot or opening 12 at the edge of the base plate 1. The opening 12 is of C-shape, having a narrow gap 13 at the edge of the base plate 1 and opening to an enlarged circular portion 14. The enlarged portion 14 of the opening 12 is substantially larger than the diameter of the catheter 4 so that the site where the catheter emerges from the skin can be viewed clearly through the opening. The gap 13 may be about the same size or slightly smaller than the external diameter of the catheter 4 so that it has to be compressed slightly to be pushed sideways through the gap. Midway along its length, the surface of the channel 11 is interrupted by an array of small protrusions 15, forming a locating region 16 extending along the channel.

At the end of the base plate 1 opposite the hinge 3, there is an integral catch 20 of generally L shape in section. The catch 20 has a vertical stem 21 resiliently joined with the main part of the base plate 1 at its lower end. The stem 21 supports a horizontal finger plate 23 extending outwardly from the stem to the edge of the base plate 1 and raised a short distance above the upper surface of the plate. The inner edge of the finger plate 23 projects a short distance inwardly beyond the stem 21 where it is shaped into a downwardly-projecting tooth 24.

The lid 2 has a generally inverted dish shape with a concave underside 25 conforming to the upper surface 10 of the base plate 1, and having a peripheral, downwardly-extending wall 30. The wall 30 is interrupted by a V-shape slot 31 where it aligns with the right-hand end of the channel 11. The lid 2 also has a square opening 32 in one side, opposite the hinge 3, in alignment with and slightly wider than the catch 20, the opening having an edge 33 located to be engaged by the tooth 24 on the catch.

The lid 2 is completed by gripping means 34 projecting down from its underside 25 and located in alignment with the locating region 16 on the base plate 1. The gripping means 34 is provided by five rectangular teeth 35 extending parallel to one another and transversely of the channel 11, and being spaced from one another along the locating region 16.

The retainer is secured to the skin of the patient by a ring of adhesive material (not shown) fixed to the underside of the base plate 1. The ring of adhesive extends around the circumference of the underside of the base plate 1 except in the region of the opening 12 and the catch 20. Before use, the adhesive is protected by a sheet of removable release paper, in the conventional manner.

In use, the patient end of the epidural catheter 4 is inserted into the epidural space in the usual way. The catheter 4 is then secured with the retainer by pushing it sideways through the gap 13 into the opening 12 where it can be moved freely along its length. After removing the adhesive release paper, the base plate 1 is stuck to the skin with the enlarged part 14 of the opening 12 located directly above the site of entry of the catheter through the skin. The catheter 4 is bent down along the channel 11 in the base plate 1 and held where it projects beyond the base plate. The lid 2 is then folded down until the tooth 24 on the catch 20 engages the edge 33 on the lid, thereby retaining the lid closed. With the lid 2 closed, the machine end of the catheter 4 emerges from the retainer through the slot 31 in the lid. In the closed position, the teeth 35 bear against the upper surface of the catheter 4, urging it against the locating region 16 on the base plate 1 and gripping the catheter firmly. The spacing between the teeth 35 and the locating region 16 is such that the wall of the catheter 4 is compressed slightly but the passage through the catheter is not occluded. With the lid 2 closed, the friction between the catheter 4, the lid and the channel 11 provides a secure retention of the catheter 4 so that any force applied to its machine end is not transmitted to the portion of the catheter in the body. Because the lid 2 extends over the opening 12 and the immediate portion of the catheter 4, it helps protect the site and catheter from contamination.

The lid 2 of the retainer is easily opened by pressing down on the finger plate 23 so that its outer end pivots down and the tooth 24 is lifted up out of engagement with the lid. With the lid 2 open, the large size of the opening 12 enables the clinician to inspect the site for inflammation of the skin, or to disinfect the site, without having to remove the retainer from the skin. The opening also allows distance markings on the catheter to be inspected where the catheter extends through the skin, so that the depth of insertion can be readily determined.

It can be seen that the retainer could be secured to the catheter 4 either before or after its machine end is fastened in a connector, because the machine end of the catheter does not have to be threaded through an aperture, as in some previous devices. Also, the retainer can be removed for inspection of the underlying skin, or for replacement, without the need to disturb connection with the catheter. The retainer can be made as a single-piece moulding of plastic, thereby avoiding assembly procedures and enabling the device to be made at low cost.

Figure 3:
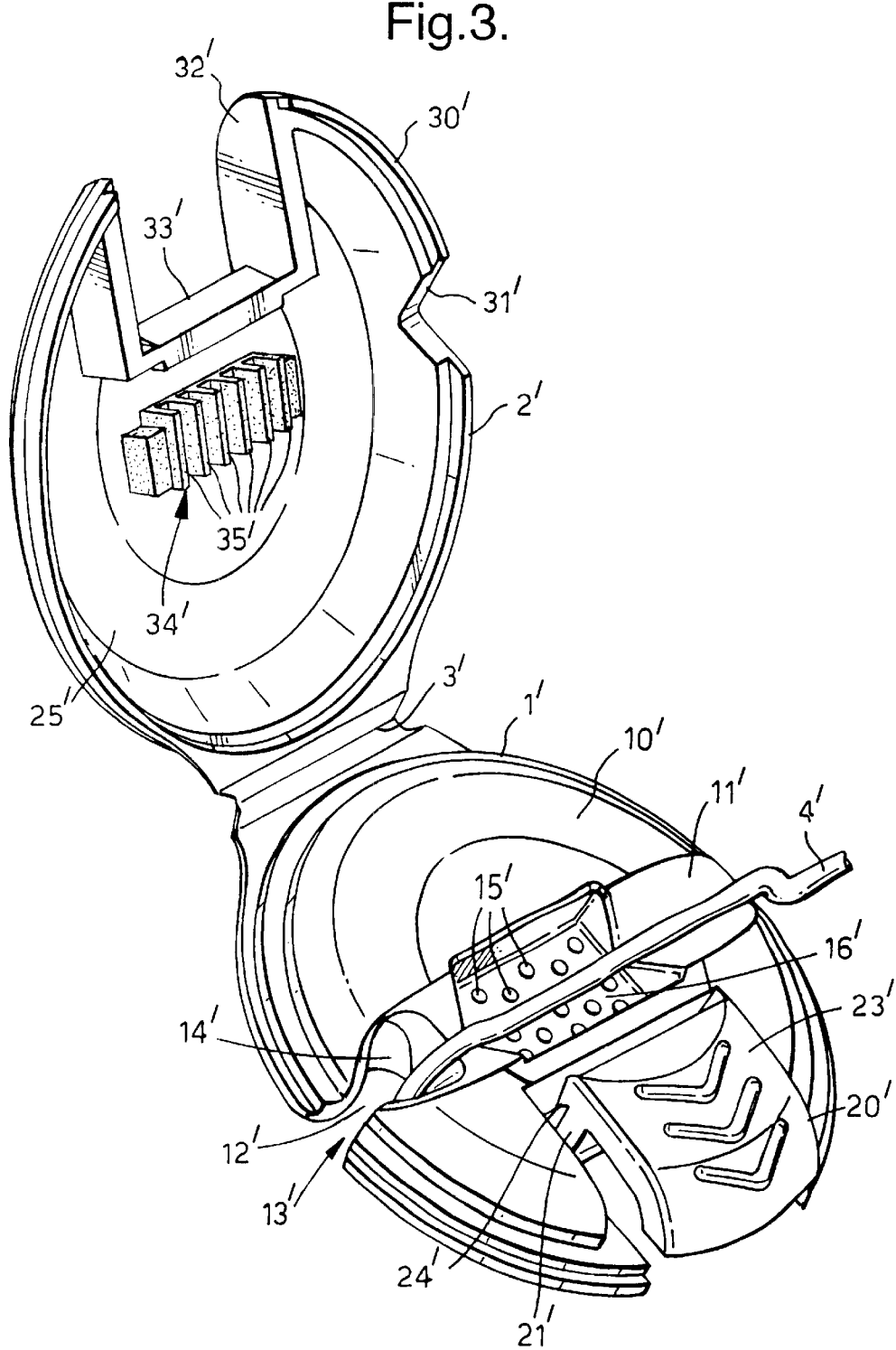
FIG. 3 is a perspective view of an alternative form of retainer.

There are various modifications that can be made to the retainer, such as shown in FIG. 3, where similar features to those in FIGS. 1 to 2 are given the same reference number with the addition of a prime '. In this modification, the gripping means 34' on the lid 2' is provided by a separate component in the form of an elastomeric rubber pad, which may have ribs 35' on its underside, as shown, or be flat. The pad 34' could be insert moulded with the lid 2' or be attached separately, such as by means of an adhesive.

Figure 4:
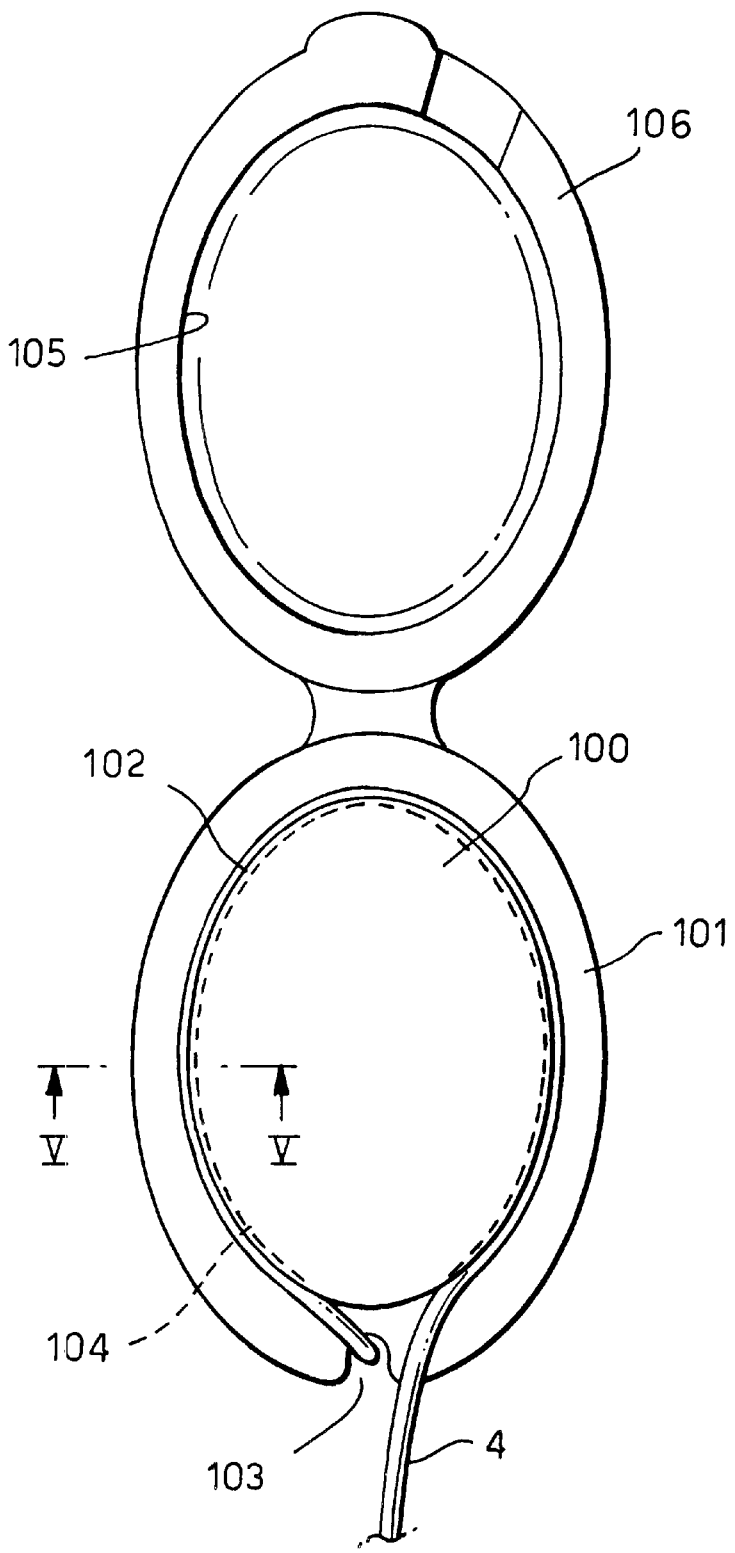
FIG. 4 is a plan view of a further form of retainer with its lid open.
Figure 5:
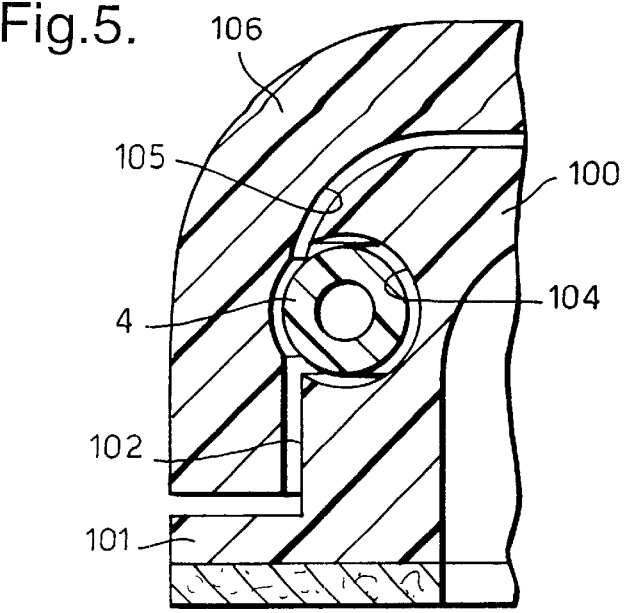
FIG. 5 is a transverse section view through a part of the retainer of FIG. 4, with its lid closed.
Figure 6:
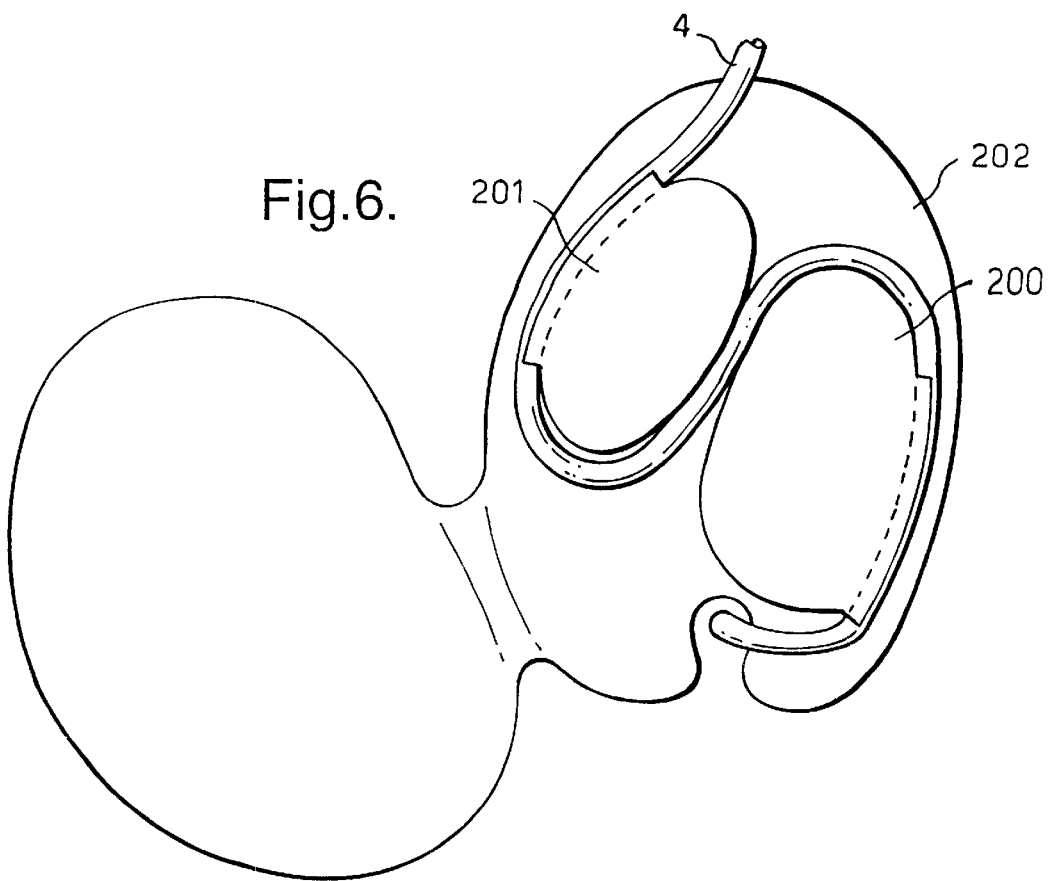
FIG. 6 is a plan view of a fourth form of retainer.

Instead, the retainer could have a central formation 100 on the base plate 101 with a curved, vertical, outwardly-facing wall 102 about which the catheter 4 is looped, as shown in FIGS. 4 and 5, to extend out of the retainer adjacent the location of the slot 103. The catheter extends in a channel 104 around the wall 102 and is retained by engagement with an inwardly-facing wall 105 on the lid 106, when this is closed. Alternatively, the retainer could have two formations 200 and 201 on the base plate 202, as shown in FIG. 6, about which the catheter 4 is looped in an S shape. In this arrangement, the friction of the catheter 4 with the formations 200 and 201 may be sufficient to retain the catheter without the need for the lid to grip it.

In various other modifications, the lid need not be hinged on about a horizontal axis but could be rotatable about a vertical axis or slidable into a closed position. The base plate could have an inwardly-facing wall against which the catheter could be fitted, the lid having a wall that extends around the wall on the base plate, on its inside, so as to engage and retain the catheter.

It will be appreciated that the retainer is not confined to use with an epidural catheter but could be used with other catheters.

What I claim is:

1. A catheter retainer, wherein said retainer is removable independently of said catheter, comprising:
   a base plate further comprising
      a lower surface disposed to attach to a patient,
      a generally dome-shaped raised upper surface,
      a peripheral surface,
      a transversely-disposed catheter channel defined in said upper surface; and
   a lid, said lid having closed and open positions and further comprises
      an inverted dish-shaped lower surface conformal to said upper surface,
      a downwardly-extending wall disposed to engage said peripheral surface of said base plate when said lid is in said closed position,
      a downwardly-opening V-slot in said wall; wherein
   said catheter channel has first and second ends, wherein said first end aligns with said V-slot when said lid is in said closed position thereby forming a first opening disposed to retain said catheter, wherein
   said second end has a C-shaped notched defining a second opening through which said catheter enters said patient, said notch being substantially wider than the diameter of said catheter, and wherein said catheter channel has a centrally-positioned locating region, and wherein said lid in said closed position completely covers said second opening.

2. A catheter retainer, wherein said retainer is removable independently of said catheter, according to claim 1, wherein said lid has gripping means on its underside such that said catheter is retained between said locating region and said gripping means.

3. A catheter retainer according to claim 2, wherein said gripping means includes a plurality of teeth.

4. A catheter retainer according to claim 2, wherein said gripping means includes a resilient pad.

5. A catheter retainer, wherein said retainer is removable independently of said catheter, according to claim 1, wherein said locating region has protrusions adapted to engage said catheter.

6. A catheter retainer, wherein said retainer is removable independently of said catheter, according to claim 1, wherein said locating region is formed in a channel in said base.

7. A catheter retainer, wherein said retainer is removable independently of said catheter, according to claim 1, including a hinge between said lid and said base.

8. A catheter retainer, wherein said retainer is removable independently of said catheter, according to claim 1, wherein said lid covers said opening when closed.

9. A catheter retainer, wherein said retainer is removable independently of said catheter, according to claim 1, wherein said locating region is located on a path that extends substantially laterally of said base such that said catheter extends laterally across said retainer substantially opposite said opening.

10. A catheter retainer, wherein said retainer is removable independently of said catheter, according to claim 1, including a catch, said catch being adapted to retain said lid closed on said base.

11. A catheter retainer, wherein said retainer is removable independently of said catheter, according to claim 1, wherein said lid and said base are a single-piece moulding.

12. An epidural catheter retainer, wherein said retainer is removable independently of said catheter, comprising:

a base plate further comprising
a lower surface disposed to attach to a patient,
a generally dome-shaped raised upper surface,
a peripheral surface,
a transversely-disposed catheter channel defined in said upper surface;

a lid, said lid having closed and open positions and further comprises
an inverted dish-shaped lower surface conformal to said upper surface,
a downwardly-extending wall disposed to engage said peripheral surface of said base plate when said lid is in said closed position,
a downwardly-opening V-slot in said wall; wherein said catheter channel has first and second ends, wherein said first end aligns with said V-slot when said lid is in said closed position thereby forming a first opening disposed to retain said epidural catheter, wherein said second end has a C-shaped notched defining a second opening through which said catheter enters said patient, said notch being substantially wider than the diameter of said epidural catheter, and wherein said catheter channel has a centrally-positioned locating region, and wherein said lid in said closed position completely covers said second opening;

a hinge connecting said base to said lid, parallel to said channel; and a catch adapted to retain said lid gripping said catheter in said closed position.

\* \* \* \* \*